United States Patent [19]

Boutaine et al.

[11] B 3,997,783

[45] Dec. 14, 1976

[54] METHOD FOR TESTING THE ADHESION BETWEEN THE RUBBER COMPOUND AND THE CORD FABRIC OF A PNEUMATIC TYRE

[75] Inventors: Jean-Louis Boutaine, Le Chesnay; Guy Courtois, Paris; Jean-Claude Tanguy, Athis-Mons, all of France

[73] Assignee: Commissariat a l'Energie Atomique, Paris, France

[22] Filed: Dec. 24, 1974

[21] Appl. No.: 536,082

[44] Published under the second Trial Voluntary Protest Program on March 16, 1976 as document No. B 536,082.

[30] Foreign Application Priority Data

Dec. 27, 1973 France .............................. 73.46597

[52] U.S. Cl. .............................. 250/303; 250/354; 250/363 R
[51] Int. Cl.² ......................................... G01T 1/161
[58] Field of Search .................. 250/303, 354, 363

[56] References Cited

UNITED STATES PATENTS

| 3,247,382 | 4/1966 | Schneider | 250/303 |
| 3,742,988 | 7/1933 | Kush | 250/303 |

*Primary Examiner*—Harold A. Dixon
*Attorney, Agent, or Firm*—Sughrue, Rothwell, Mion, Zinn & Macpeak

[57] ABSTRACT

In a method for determining whether a used tyre exhibits zones of detachment between the rubber compound and the cord fabric or zones of substantial porosity, a radioactive gas which emits gamma-rays is injected under pressure into the tyre in the zone corresponding to the layers of textile fibers which constitute the cord fabric. The gas is allowed to diffuse within the interior of the tyre and to accumulate at the defective points, whereupon the radiation emitted at least at one point of the tyre is detected.

9 Claims, 7 Drawing Figures

METHOD FOR TESTING THE ADHESION BETWEEN THE RUBBER COMPOUND AND THE CORD FABRIC OF A PNEUMATIC TYRE

This invention relates to a method for testing the adhesion between the rubber compound and the cord fabric of tyres (tires), especially tubeless tyres and aircraft tyres.

In a new tyre, it can be established that perfect adhesion exists between the rubber compound and the cord fabric reinforcement which is placed on the inside of the tyre body. On the other hand, it is observed in a worn tyre and especially in zones of maximum fatigue that the rubber compound exhibits local and/or general porosity and that defects in adhesion between the cord fabric and the rubber compound are also present.

In order to reduce the danger of bursting of tyres, it is therefore desirable before retreading the tyres to detect whether they exhibit zones of detachment between the rubber compound and the fabric or zones of substantial porosity.

The needle method is commonly employed for this purpose and consists in injecting air under pressure into the interior of tyres by means of a needle and in detecting any presence of local swellings by measuring the variations in thickness of the tyres.

In point of fact, this method gives only approximate readings and is consequently unreliable.

This invention is directed to a method for determining whether a used tyre exhibits zones of detachment between the rubber compound and the cord fabric or zones of substantial porosity. The method is distinguished by the fact that a radioactive gas which emits gamma-rays is injected under pressure into the body of the tyre in the zone of the layers of textile fibers which constitute the cord fabric, said gas is allowed to diffuse within the body of the tyre and to accumulate at the defective points, whereupon the radiation emitted at least at one point of the tyre is detected.

The injected gas progresses fairly rapidly within the cord fabric along this latter and more rapidly as the degree of wear is greater, and the gas pockets formed at the points which exhibit defects are detectable for several days. Advantage is derived from the fact that the gas injected under pressure does not escape through the admission orifice when the injection needle is withdrawn, which is an unexpected result.

This method can be carried into effect by means of an apparatus which essentially comprises a $\gamma$-emitting gas injector and a detector, the injector being fitted with a device for obtaining a suitable mixture of a $\gamma$-emitting gas and an inert gas, said device being associated with an injection trocar, the detector being fitted with a scintillation probe, a scintillometer, a counting ratemeter and a recorder. Suitable detectors for this purpose are the scintillation probes, proportional counters, Geiger counters, ionization chambers, semiconductors, photographic emulsions.

By virtue of the means thus employed, it is possible to gain an idea on the one hand of the fatigue of tyres and on the other hand of the presence of adhesion defects between cord fabric and rubber compound within the plies as a result of the presence of zones of accumulation of tracer gas.

In the case of a tyre which does not exhibit local defects, the ratio of the count rates $R_{MIN}$ taken at 180° with respect to the point of injection at $R_{MAX}$ taken at the level of the injection point is a measurement of the total porosity or of the fatigue of the tyre.

$$\text{Thus } \tau_G = \frac{R_{MIN}}{R_{MAX}} = 0$$

in the case of a new tyre

When the fatigue of the tyre increases, $\tau_G$ rises and at a maximum $$\tau_G = \frac{R_{MIN}}{R_{MAX}} = 1$$

in the case of a "totally" porous tyre. At the level of a flaw, the extent of the flaw can be measured by the ratio:

$$\tau_D = \frac{R_D}{R'_D}$$

$R_D$ being the real count rate at the point of the flaw, $R'_D$ being the virtual count rate which would be recorded at the same point with respect to the point of injection in a tyre of the same type which exhibits total fatigue of the same magnitude.

The criteria which govern acceptance or rejection of tyres at the time of inspection can be based on maximum values of $\tau_D$ and/or of $\tau_G$ which should not be exceeded.

Curves giving the value $RD/R_{MAX}$ can also be plotted in order to gain both a general and precise idea of the fatigue of the tyre as well as the existence and magnitude of point defects if these curves have local maximums.

In order to ensure suitable utilization of the method, the tracer gas employed must have the following characteristics:

the energy of the emitted gamma photons must not exceed 100 kev;
the half-life of the radioelement must be sufficient to ensure supply, injection and detection under good conditions and must not be too long to permit rapid re-use of inspected tyres; in practice, said half-life must be within the range of few hours to a few days;
the biological half-life of the radioelement must be as short as possible in order to limit the dangers of contamination of operators;
the chemical nature of the tracer gas must be such that the behavior of this latter is as inert as possible with respect to the tyre components. The two conditions just mentioned are wholly satisfied by the radioactive rare gases.

In practice, the tracer gases which can be employed are nitrogen and the rare gases mixed with gases such as:

| | | |
|---|---|---|
| $Xe^{133}$ | T = 5.4 d | $\gamma$-emitter of 81 keV (37 %) |
| $CH_3Br^{82}$ | T = 35.3 h | $\gamma$-emitter (many lines in the 554 to 1475 keV range) |
| $A^{41}$ | T = 1.43 h | $\gamma$-emitter of 1293 keV (99 %). |

Xenon is chemically inert, is rapidly eliminated from the body and commends itself as the most suitable gas.

The pressure at the injection and the duration of said injection must be sufficient to ensure that the tracer gas diffuses to the measuring point in sufficient quantity. The pressure must be lower than or equal to 12 bars and the duration must be of the order of a few minutes.

Irrespective of the type adopted, the detector must be carefully collimated by means of a collimator of metal having high density such as lead, tungsten or depleted uranium and must be applied as closely as possible in contact with the surface to be scanned in order to improve the sensitivity of detection in regard to both contrast and definition.

When scanning is performed on the outer face of the tyre, provision can advantageously be made for an internal shield placed in contact with the internal face of the tyre and conforming as closely as possible to the internal shape of this latter in order to improve the sensitivity of detection and to prevent any mutual influence of the sidewalls.

Further properties and advantages of the invention will in any case be brought out by the following description of one example of application of the method of testing, reference being made to the accompanying drawings, in which.

Figure 1A:
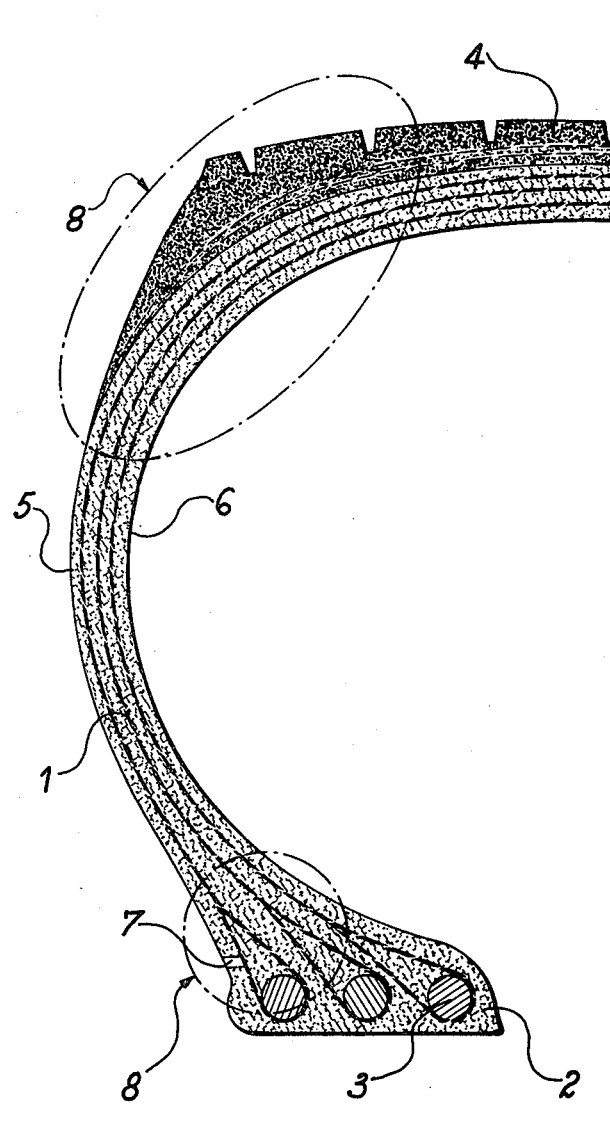
FIGS. 1a and 1b are part-sectional views of a tubeless aircraft tyre.
Figure 1B:
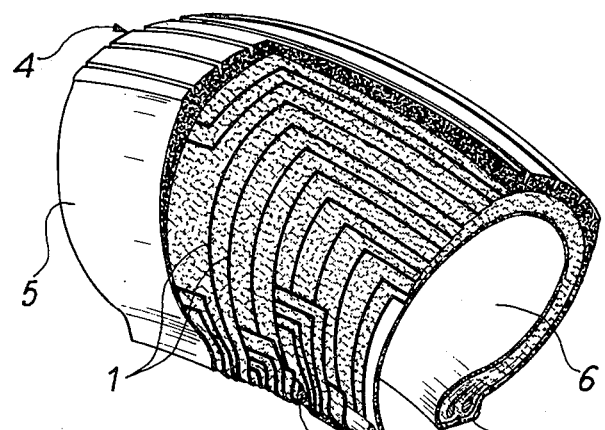

The tyre body which is seen in FIGS. 1a and 1b is constituted by a casing formed of several layers of cord fabric 1 consisting of impregnated synthetic fibers. These layers or plies are embedded in the rubber compound of the tyre bead 2 and their edges are folded over bead wires 3 placed within the tyre bead.

The outer surface of the tyre casing is protected by a thickness of rubber so that the crescent includes the central tread 4 which is extended on each side to form a sidewall 5.

Consideration being given in this example to a tubeless tyre, the inner tube is accordingly replaced by a leak-tight liner 6 of special rubber compound which is integral with the tyre body.

Impermeability of the liner 6 is not absolute. Under the action of the internal pressure, the air diffuses and accumulates within the cord elements which make up the tyre casing. In order to discharge this residual air over the entire periphery of the sidewalls up to approximately one-third of the thickness of the tyre casing, the tyres are pierced by vents 7 which are located near the bead and spaced apart at a distance of approximately 75 mm.

If air is injected into a tyre of this type which has already been used, through a vent or through a hole located in the vicinity of a vent, the air escapes two or three minutes later through the hole which is located diametrically opposite. This shows that the internal zone becomes porous and permits the accumulation of air or of any other gas.

When the tyre tread is worn, it is possible to reconstitute or retread the tyre by brushing the tread suface and then depositing a fresh layer of rubber on this latter. Two plies of cord elements of synthetic fibers are embedded in the rubber compound which has thus been deposited. These plies are separate and independent of each other.

Used tyres have to be carefully inspected for safety reasons. In particular, the two zones 8 of maximum deformation are subject to deterioration and are liable to exhibit detachment of the cord elements from the rubber compound. If this defect remains undetected, the tyre is liable to burst after retreading either during initial take-off or on landing.

The injector which can be seen in FIG. 2 comprises a nitrogen cylinder 10 fitted with an expansion-valve pressure gauge 12 which is set at a pressure below or equal to 12 bars, the best results having in fact been obtained at 8 bars. The expansion-valve pressure gauge is connected through a flexible hose 13 and a valve 14 to a mixer 15 fitted with a pressure gauge 16. A striker-pin 20 and an ampoule 21 containing 3 cm³ of commercially available xenon-133 is placed within the mixer 15 which communicates through the valve 17 and the flexible hose 18 with a reservoir 19 containing the gas to be injected. The reservoir 19 is connected to a trocar 21a by means of the flexible tube 22 and the valve 23.

Figure 3:
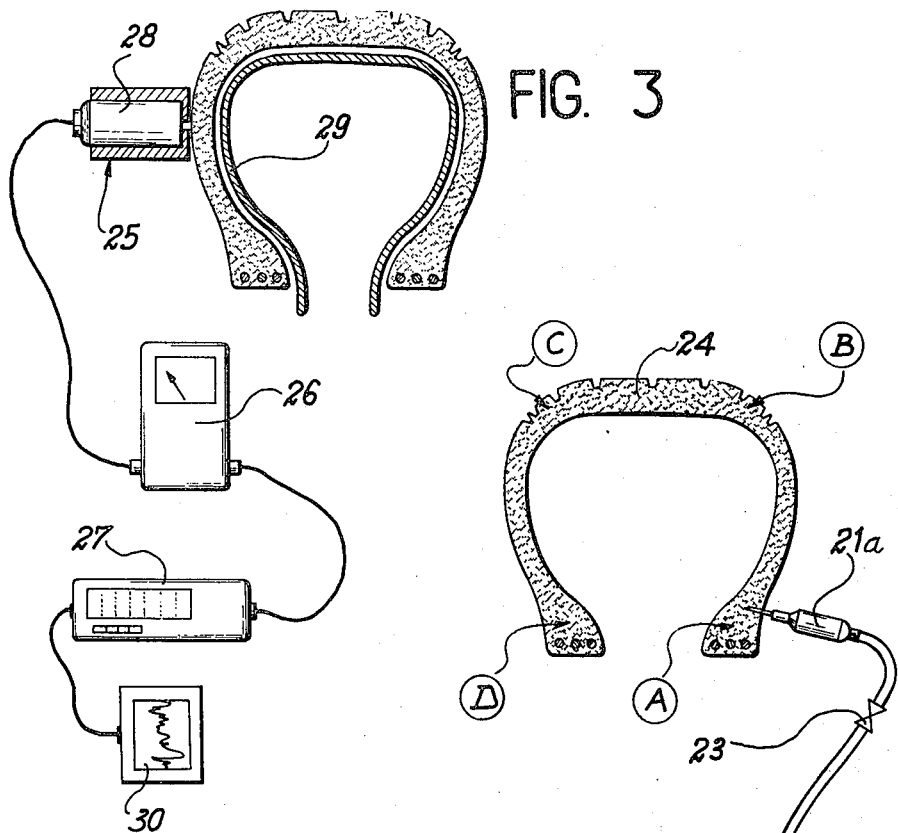
FIG. 3 is a diagram of the radioactive gas detector.

The tyre 24 to be inspected is mounted vertically on a frame (not shown) and capable of rotating about its own axis whilst the detector is stationary and continuously directed towards the tyre. The detector which appears in FIG. 3 comprises a scintillation probe 25 of type SGS 50 having an aluminium window fitted with a thallium-doped sodium iodide crystal and connected to a scintillometer 26 of type SPD 3 marketed by the Saphymo-Stel Company, which is in turn connected to a counting ratemeter 27 and to a recorder 30.

The tests were performed:
either by means of a probe alone
or by means of a probe fitted with a cylindrical lead collimator 28 having a height of 100 mm and a thickness of 5 mm,
or by means of the same collimator and by fitting inside the tyre an internal shield constituted by a lead sheet 29 having a thickness of 3 mm and corresponding to the shape of the tyre.

Figure 2:
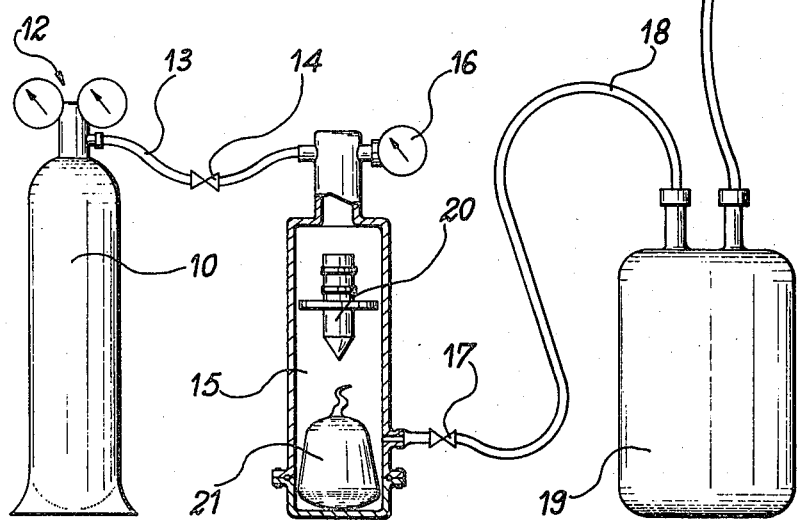
FIG. 2 is a diagram of the radioactive gas injector.

Scanning was performed in the rings designated in FIG. 2 by the references A, B, C and D, the probe being at right angles to the surface of the tyre.

The operation of this apparatus is as follows.

At the beginning of each test, the valve 14 is closed. The mixer 15 and the reservoir 19 are at atmospheric pressure. The valves 17 and 23 are closed. The striker-pin 20 is set. The xenon ampoule 21 is placed within the mixer and this latter is closed. The valve 14 is opened. Under the action of the pressure of nitrogen, the striker-pin is driven downwards and breaks the ampoule.

It is ascertained that the pressure rise to 8 bars within the mixer 15.

The valve 17 is then opened, whereupon the nitrogen drives the xenon into the reservoir. It is ascertained that the pipe between the mixer and the reservoir contains an active gas mixture. The valves 17 and 14 are closed when the pressure is again at 8 bars.

There is then available a reserve supply of 3 liters of a gas mixture consisting of nitrogen and xenon-133, a predetermined quantity of which is introduced by means of the trocar 21a.

In order to carry out the different measurements which are necessary for inspection and testing of the tyre, the detector is displaced along a guide (not shown in the drawings) and the tyre is rotated in a vertical plane.

It has been possible by means of this apparatus to test a tubeless tyre fitted on the main landing-gear of a three-engined or four-engined civil transport jet aircraft with a gas mixture of nitrogen and xenon-133 having an activity concentration of 3 mCi calculated at 8 bars, which corresponds to an activity concentration of 0.375 mCi per liter at normal temperature and pressure, the mixture being injected through a single hole at a pressure of 8 bars for a period of 5 minutes.

Figure 4:
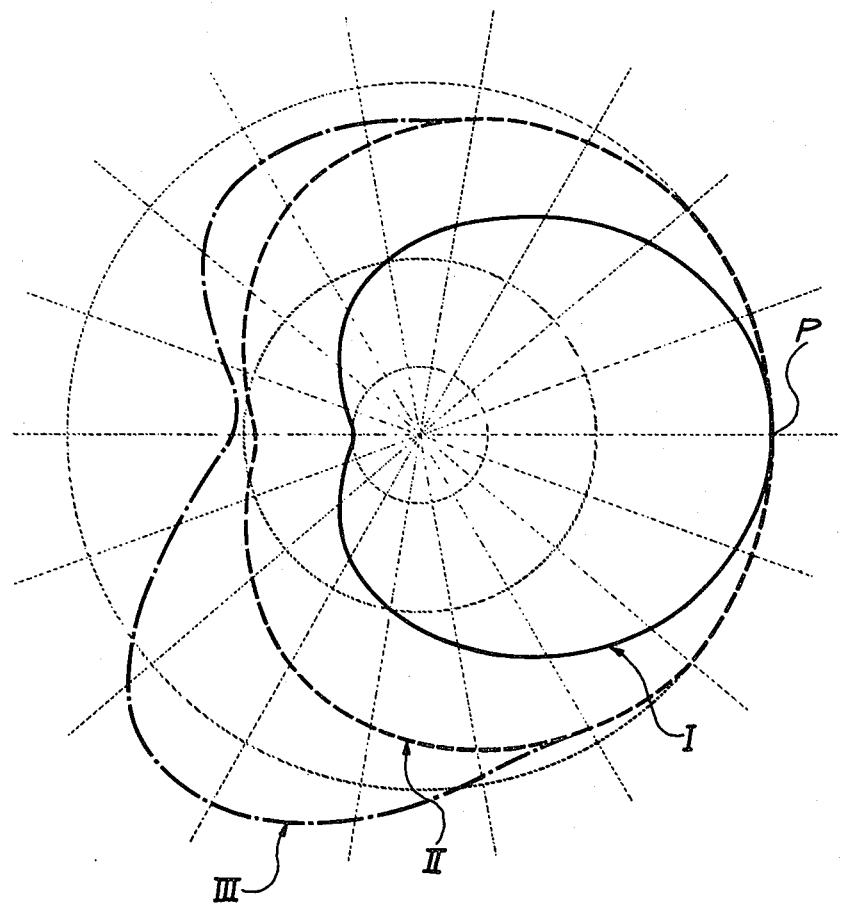
FIG. 4 shows curves of variation in polar coordinates of the relative count rates $RD/R_{MAX}$ obtained on more or less worn tyres; these count rates give the distribution of the tracer gases.

The curves of distribution in polar coordinates of the count rates represented in FIG. 4 have been plotted by means of a probe fitted with a collimator and with an internal tyre shield, a single injection having been made at the point P.

Curve I relates to a tyre which exhibits little wear and is free from defects, curve II relates to a tyre which exhibits a medium degree of wear without any defect and curve III relates to a tyre having medium wear and exhibiting defects.

Figure 5:
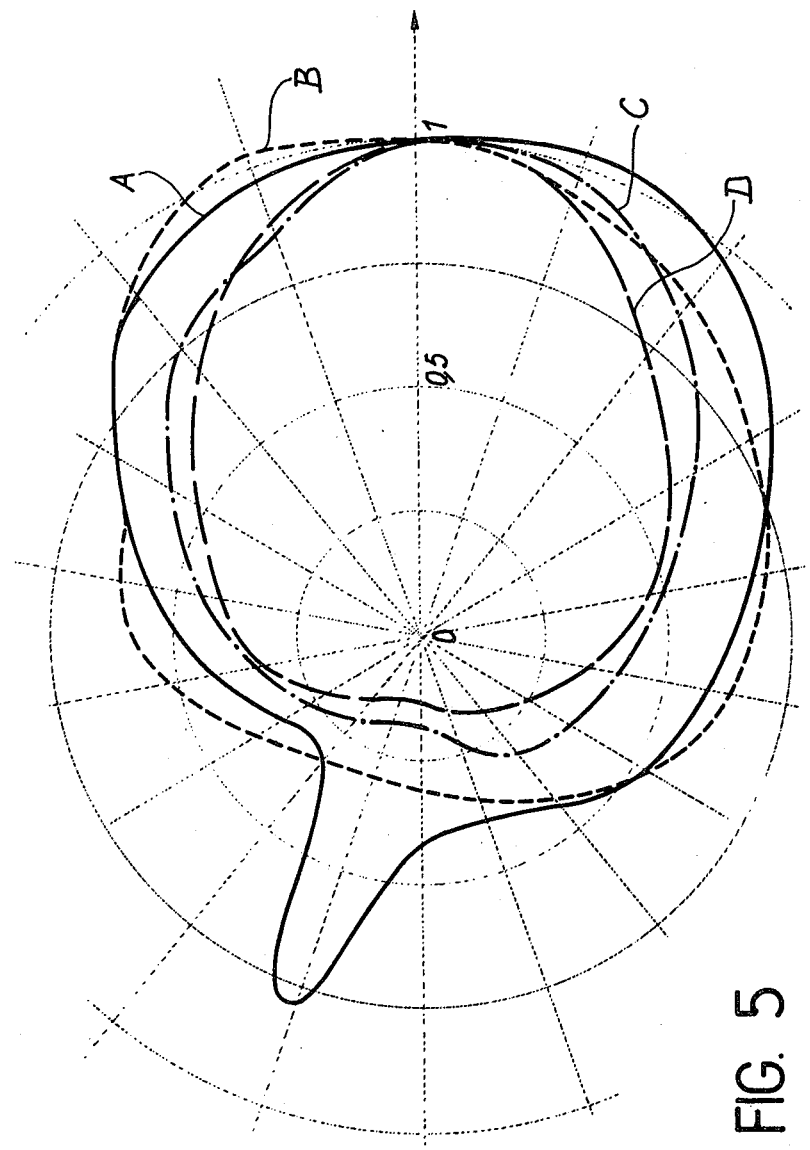
FIG. 5 shows similar curves obtained in the case of a single tyre by scanning four circumferences in the zones A, B, C, D indicated in FIG. 2 after simultaneous injections at points located on a given transverse section within the zones A and D.

In FIG. 5, curve A has a peak which represents the existence of a defect at approximately 160° with respect to the injection point P.

Figure 6:
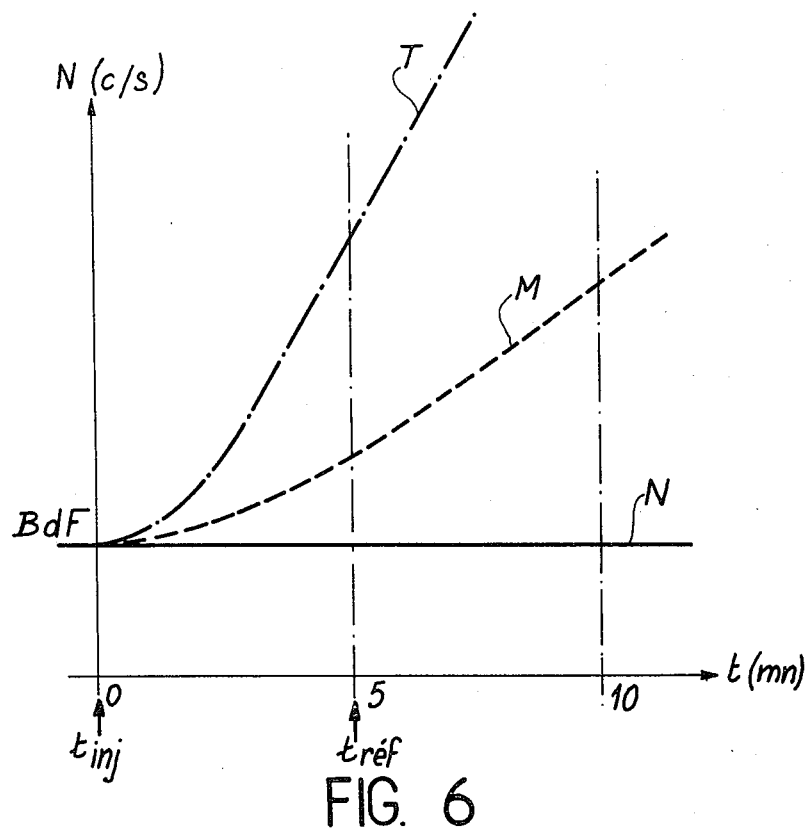
FIG. 6 shows curves which give the count rate at 180° from the point of injection and measured during the injection as a function of time in the case of three tyres of the same type.

The injection of radioactive gas can be performed in one or a number of holes located in a single cross-section of the tyre. In order to have sufficiently high count rates in a fairly short time in the case of a tyre which shows only slight wear, it is accordingly an advantage to perform two injections in the sidewalls of the tyre in the high-fatigue zones A and D. If a collimated probe is placed during the injection at a point of the cross-section which is diametrically opposite to the first on the same sidewall of the tyre, there are thus obtained counting curves of the type which appear in FIG. 6 and give $N_{180}$ as a function of time.

This count rate $N\alpha$ is advantageously measured at 180° from the point of injection in order to obtain the highest degree of accuracy but this is not a stringent requirement and said count rate may in fact be measured at any desired point.

In the case of new or very slightly worn tyres, there is no increase in the count rate and this latter remains equal to the background count (for example 15 to 35 c/s in the case of $N_{180}$ with the equipment used for performing the tests), even while maintaining the pressue over a period of 30 minutes for example, as is shown by the curve N.

On the other hand, a significant increase in the count rate is observed in a tyre which exhibits medium wear (curve M) or a high degree of wear (curve T). $N_{180}$ can attain 100 to 200 c/s at the end of 5 minutes of injection if a nitrogen-xenon mixture having a concentration of 3 mCi of xenon-133 per liter of mixture is injected at a pressure of 8 bars, namely 0.375 mCi/l at normal temperature and pressure.

During tests performed on four different types of aircraft tyres ranging from new tyres to tyres which had been retreaded ten times, it has been observed that:

a. there is no increase in the count rate in new tyres;

b. in the case of worn tyres of the same type, there exists a good correlation between curves which give $N_{180}$, that is to say the number of counts per second detected at a point located at 180° from the point of injection as a function of $t$ and the degree of fatigue (in particular the number of retreads performed on the tyre under normal conditions of service between each retreading operation);

c. in the case of a given population of tyres (same manufacturer, same retreader, same number of retreads, same use), there exists a close correlation between the shape of the curves which give $N_{180}$ as a function of $t$ and the value $\tau_G$ as defined at the beginning of this description.

In other words and in the case of a given tyre of this population, if $\tau_G$ is distinctly higher than the mean value $\bar{\tau}_G$ of the tyres of this population, the curve which gives $N_{180}$ in the case of this element is distinctly more steeply inclined than the mean curve.

Moreover, it is particularly important to note that the presence of a large flaw in the tyre results simultaneously in a value of $\tau_G$ which is higher than the mean value $\bar{\tau}_G$, and a steeper slope of the curve which gives $N_{180}$ as a function of $t$.

Simple measurement of $N_{180}$ at the end of a predetermined time interval $t$ therefore permits a quality test which records both the state of general fatigue and the possible existence of local defects. The presence of such defects can be established if they are substantial simply by comparison with the values of $N_{180}$ of tyres of a population which has the same state of general fatigue.

What we claim is:

1. A method for determining whether a used tyre exhibits zones of detachment between the rubber compound and the cord fabric or zones of substantial porosity, wherein a gamma-ray emitting radioactive gas is injected under pressure into the body of the tyre in the zone of the layers of textile fibers which constitute the cord fabric, said gas is allowed to diffuse within the interior of the tyre and to accumulate at the defective points, and the radiation emitted at least at one point of the tyre is detected.

2. A method according to claim 1, wherein the injection of the radioactive gas is performed through holes located at any points of the surface of the tyre.

3. A method according to claim 1, wherein the injection of the radioactive gas is performed through vents located near the tyre bead.

4. A method according to claim 1, wherein the injection of the radioactive gas is performed through one or a number of holes located in the same cross-section of the tyre and the detection is performed after each injection by rotating the tyre about its own axis in a vertical plane, the detector or detectors being continuously directed towards the tyre during its rotation.

5. A method according to claim 1, wherein the radioactive gas employed is selected from xenon-133, methyl bromine $CH_3Br^{82}$, argon-41.

6. A method according to claim 1, wherein the injection is performed at a pressure below or equal to 12 bars for a period of a few minutes.

7. A method according to claim 6, wherein the pressure is equal to 8 bars.

8. A method according to claim 1, wherein use is made of a shield which closely conforms to the internal shape of the tyre.

9. A method according to claim 1, wherein the injection is performed through one or a number of holes located in the same cross-section of the tyre and wherein the detection is performed simultaneously at one point of the cross-section which is approximately diametrically opposite to the first.

* * * * *